United States Patent [19]

Sanborn et al.

[11] 4,232,025

[45] Nov. 4, 1980

[54] POLYMERIC INSECTICIDAL COMPOSITIONS OF MATTER

[75] Inventors: James R. Sanborn; Charles H. Tieman, both of Modesto, Calif.

[73] Assignee: Shell Oil Company, Houston, Tex.

[21] Appl. No.: 36,630

[22] Filed: May 7, 1979

[51] Int. Cl.$^3$ .................... A01N 9/22; C07D 279/04
[52] U.S. Cl. .................................. 424/256; 536/20; 544/53
[58] Field of Search .................... 544/53; 424/256; 536/20

[56] References Cited

U.S. PATENT DOCUMENTS 3,993,648  11/1976  Powell ................................. 544/53

OTHER PUBLICATIONS

Hartley et al., Chem. Abstracts, vol. 51, col. 2226d (1957), (abst. of U.S. Pat. No. 2,759,300).
Kaputskii et al., Chem. Abstracts, vol. 85, Abst. 130,433j (1976).

*Primary Examiner*—John D. Randolph

[57] ABSTRACT

Reaction products of tetrahydro-2-(nitromethylene)-2H-1,3-thiazine and certain oxidized polysaccharides, useful as insecticides.

6 Claims, No Drawings

POLYMERIC INSECTICIDAL COMPOSITIONS OF MATTER

DESCRIPTION OF THE INVENTION

It has been found that useful insecticidal properties are possessed by the reaction products of tetrahydro-2-(nitromethylene)-2H-1,3-thiazine and oxidized polysaccharides that contain at most only minor amounts of the carboxyl moiety.

To avoid repetition of its long chemical name, tetrahydro-2-(nitromethylene)-2H-1,3-thiazine will be referred to hereinafter as "Compound I." It is a known compound; it, and a method for preparing it, are described in U.S. Pat. No. 3,993,648.

The precise chemical character of the subject reaction products has not been established, because: (1) the products are insoluble, so that solution nuclear magnetic resonance spectra could not be obtained; (2) the structure of the oxidized polysaccharide precursor is not known in any detail, but contains aldehyde moieties, and/or moieties which react as do aldehyde moieties, and (3) Compound I can react with an aldehyde moiety in several different ways to give different kinds of products.

The polysaccharide precursors are those materials commonly known in the art as periodate-oxidized polysaccharides, or simply as oxidized polysaccharides. Their general chemical character is described in Barry and Mitchell, U.S. Pat. No. 2,885,394 and Rowen et al., J. Am. Chem. Soc., 73, 4484–7 (1951).

As a class, these oxidized polysaccharides can be characterized as the products which result from the treatment of a polysaccharide with a periodate. This treatment results in a modification of the polysaccharide structure such that the product reacts in some cases as if it were a poly-aldehyde. It is believed that the reactive moieties are in fact "hydrated" aldehyde moieties, and/or hemiacetal or acetal moieties.

The degree of oxidation is readily controlled, and is defined as the degree to which hydroxy moieties in the polysaccharide structure are converted to aldehyde moieties (or their equivalent)—i.e., from 0% to 100% oxidized. For the purposes of this invention, the polysaccharide should be at least 50% oxidized, and preferably is at least 90% oxidized.

Suitable polysaccharide precursors are the plant-derived polysaccharides, such as celluloses, hemicelluloses (pentosans, such as xylan), starches (including both amylose and amylopectin, and soluble starch), dextrans, dextrins, inulins, algins, and gums.

Preferred oxidized polysaccharides are the oxidized starches and oxidized microcrystalline cellulose. Regarding these latter materials, the microcrystalline cellulose precursors are well known, also being designated as "level-off D.P. (for degree of polymerization) celluloses": D.A. Battesta, Ind. and Eng. Chem., 42, 502–7 (1952); U.S. Pat. Nos. 2,978,446, 3,539,365. (In the processes of these patents, the microcrystalline cellulose is comminuted to form even smaller particles.) The latter patent is drawn to microcrystalline cellulose in combination with sodium carboxymethylcellulose, which aids in improving the dispersibility of the cellulose. Such products also are suitable as precursors or the reaction products of this invention, as are microcrystalline celluloses that have been pretreated to increase their dispersibility, provided that the pretreatment has not interfered with the reactivity of the cellulose.

In forming the products of this invention, the oxidized polysaccharides react as if there were only one aldehyde moiety per each of its repeating units, presumed to be the following structure:

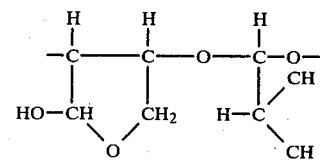

It is theorized that in the oxidized polysaccharides the primary moiety is the acetalhydrate in which the hydrated carbonyl moiety is much more reactive than the cyclic acetal moiety. Thus, the reaction products contain at most about 0.5 molar equivalent of Compound I per repeating unit of the oxidized polysaccharide. To attain the highest level of insecticidal activity possible, the product should contain at least 0.35—and preferably contains at least 0.40—molar equivalent of Compound I per repeating unit of the oxidized polysaccharide. Because their precise chemical character is not known, the moieties in the product which were derived from Compound I are referred to herein as the "equivalent" of Compound I.

Since the molecular weight of Compound I and the repeating unit of the oxidized polysaccharide are nearly the same, the weight of the moieties present in the products of this invention which have been derived from Compound I will amount to no more than about fifty percent of the weight of the product and to attain the highest level of insecticidal activity possible, the product will contain at least 35 percent and preferably contains at least 40 percent by weight of the equivalent of Compound I.

To attain the objectives of this invention, the oxidized polysaccharides must contain no more than a minor amount of the carboxyl (—COOH) moiety, for the insecticidal activity of the product appears to fall as the amount of carboxyl groups in the oxidized polysaccharide increases. Thus, the product prepared from alginic acid had poor insecticidal activity, as did the product prepared from an "overoxidized" starch.

It appears that the lower the degree of cross-linking in the oxidized polysaccharide, the higher the insecticidal activity of the product. Thus, it usually will be found desirable to use a freshly oxidized polysaccharide (cross-linking in the oxidized polysaccharide appears to occur to some extent with time). Further, oxidized polysaccharides in which the polysaccharides contain less cross-linking—such as starches and microcrystalline celluloses—generally will be preferable to those containing more cross-linking—such as amylopectin.

The products of this invention are generally yellow solids essentially insoluble in water and common oxygenated solvents such as acetone. It has been found that in these products the insecticidal activity generally is related to the physical form of the product, small particles of the product being more active than larger masses, the insecticidal activity increasing as the particles become smaller. Accordingly, it is preferred that the products be in the form of particles not exceeding about 100 microns in their largest dimension, with even smaller particles—of the order of 40 microns or less, being even more preferable.

The products of the invention are readily prepared by simply stirring a mixture of Compound I, the oxidized polysaccharide, and water, at room temperature until the reaction is complete—which may require from one-half day to ten days, or longer in some cases.

The product is readily recovered and isolated by filtering the reaction mixture and washing the resulting crude solid product with water, then with methanol, and drying it.

Since the oxidized polysaccharides react as if one aldehyde moiety is present per repeating moiety therein, the amount of Compound I to be used is readily determined: at least one mole of Compound I is used per repeating moiety in the oxidized polysaccharide.

A catalyst, such as a small amount of a mineral acid, may be employed to increase the reaction rate, or a buffering agent, such as sodium bicarbonate, may be employed.

Preparation of specific individual species of the products of the invention in specific instances are shown, for illustration, in the following examples.

EXAMPLE 1

A suspension of 1.6 g of a commercial oxystarch (12% water; 1.4 g oxystarch) in 25 ml of water and 2 drops of concentrated sulfuric acid was heated on a stream bath for 1 hour. Then 3.2 g of Compound I was added. The mixture was stirred at room temperature for approximately 18 hours, then filtered to give 2.8 g of the reaction product (1), as yellow solid. Sulfur analysis indicated that the product contained the equivalent of 40% of Compound I.

The oxystarch used was a commercially available oxidized corn starch, at least 90% oxidized, in the form of small particles of size varying from 60 mesh to smaller than 200 mesh, containing a maximum of 12% moisture.

EXAMPLE 2

3.2 g of Compound I and 10.7 g of a commercial aqueous dispersion of oxystarch (containing 1.6 g of the oxidized corn starch of Example 1) were mixed and the mixture was stirred at room temperature for 5 days. A tar that formed was separated and triturated first with water, then with methanol. The resulting powder was washed with methylene chloride, leaving 2.4 g of the reaction product (2), as a tan solid. Sulfur analysis indicated that the product contained the equivalent of 47% of Compound I.

The oxystarch used was a commercial product: an aqueous cationic dispersion formed by the reaction of 3% of the carbonyl moieties of the oxystarch of Example 1 with Girard T reagent ((carboxymethyl)trimethylammonium chloride hydrazide). The dispersion contained 15% of the oxystarch of Example 1.

EXAMPLE 3

100 g of corn starch, 1855 ml of water and 145 g of sodium periodate were mixed in the dark and under nitrogen, and the mixture was stirred in the dark, under nitrogen, at room temperature, for 4 days. The mixture was filtered. The filter cake was washed thoroughly with water, then with methanol. The resulting solid was dried under reduced pressure overnight, to give 98.2 g of oxystarch (3A), as a white solid.

20 g of Compound I, 156 ml of water and 10 g of 3A were mixed and the mixture was stirred at room temperature, in the dark, under nitrogen, for 6 days. The mixture then was filtered. The filter cake was washed with water, then with methanol. The resulting yellow solid was dried under reduced pressure overnight; yield: 15.3 g of the reaction product. The product was sifted through a 38 micron sieve to give 12.8 g of product (3), average particle size: 20.9 microns. Sulfur analysis indicated that the product contained the equivalent of 44% of Compound I.

EXAMPLE 4

2.5 g of Compound I was treated with 5 g of 3A according to the procedure described in Example 3. The reaction product was ground by mortar and pestle, and sieved through a 37 micron screen to give 2.9 g of 4, average particle size: 16.2 microns, containing the equivalent of 27% of Compound I.

EXAMPLE 5

1.6 g of Compound I was treated with 1.6 g of 3A in the manner described in Example 3, except that 0.4 g of sodium bicarbonate was added to the reaction mixture.

The product (5) had an average particle size of 17.2 microns and contained the equivalent of 37.5% of Compound I.

EXAMPLE 6

1.6 of Compound I was treated with 1.6 g of 3A in the manner described in Example 3, except that one drop of concentrated sulfuric acid was added to the reaction mixture.

The product, (6), had an average particle size of 15.4 microns, and contained the equivalent of 42% of Compound I.

EXAMPLE 7

Rice starch was oxidized in the manner described in Example 3 for oxidation of corn starch. 1.6 g of the resulting oxystarch was treated with 3.2 g of Compound I by the procedure described in Example 3. The product, 7, had an average particle size of 9.4 microns and contained the equivalent of 41% of Compound I.

EXAMPLE 8

Soluble starch was oxidized in the manner described in Example 3 and 5 g of the resulting oxystarch was treated with 10 g of Compound I by the procedure described in Example 3. The product, 8, had an average particle size of 21.8 microns and contained the equivalent of 45% of Compound I.

EXAMPLE 9

A purified microcrystalline cellulose, sold commercially for use in chromatographic separations, was oxidized in the manner described in Example 3 and 1.6 g of the resulting oxystarch was treated to give a product, 9, having an average particle size of 15.8 microns, and containing the equivalent of 38% of Compound I.

EXAMPLE 10

A microcrystalline cellulose that had been subjected to mechanical disintegration (U.S. Pat. No. 2,978,446), containing 11% sodium carboxymethylcellulose (to aid in suspension of the cellulose: a commercial product, U.S. Pat. No. 3,539,365), was oxidized in the manner described in Example 3. The product was very difficult to filter, so the solution/slurry was placed in a dialysis tube (DIALYA-POR®, molecular weight cut-off 12,000–14,000), and water was run over the outside, for a weekend. The product was a slurry of the oxycellulose, volume about 500 ml. Sufficient of the slurry to provide 16 g of the oxycellulose was treated with 32 g of Compound I according to the procedure described in Example 3. The product, 10, had an average particle size of 20.0 microns and contained the equivalent of 43% of Compound I.

EXAMPLE 11

A reaction product, 11, average particle size of 20.7 microns, and containing the equivalent of 43% of Compound I, was prepared by the procedure described in Example 3 by reaction of 32 g of Compound I and 16 g of an oxycellulose prepared by oxidizing a commercial microcrystalline cellulose (which also had been mechanically disintegrated, as described in Example 10), in the manner described in Example 3.

EXAMPLE 12

The procedures of Example 11 were repeated, employing as the starting material a mechanically disintegrated microcellulose that had not yet been dried. The product, 12, contained the equivalent of 46.5% of Compound I.

EXAMPLES 13–17

By the above-described procedures the following further reaction products of the invention were prepared, each being defined in terms of its oxidized polysaccharide precursor, and its properties.

13—average particle size: 12.4 microns, containing the equivalent of 40% of Compound I, prepared from oxidized potato amylose.

14—average particle size: 26.1 microns, containing the equivalent of 53% of Compound I, prepared from oxidized amylopectin.

15—average particle size: 34.2 microns, containing the equivalent of 49% of Compound I, prepared from oxidized xylan.

16—average particle size: 30.4 microns, containing the equivalent of 44% of Compound I, prepared from oxidized amylose, average molecular weight: 21078.

17—average particle size: 19.9 microns, containing the equivalent of 54% of Compound I, prepared from oxidized amylose, average molecular weight: 4068.

The products of the invention are primarily of interest for controlling larvae of the corn earworm (*Heliothis zea*). They also exhibit a low level of activity with respect to such insects as the housefly and pea aphid.

The tests with respect to the corn earworm were conducted as follows: in each of several replicates, five third-instar corn earworm larvae were placed in a cage upon a cut stem broad bean plant that had been freshly and thoroughly sprayed with a formulation of the test chemical. The formulation was prepared by adding two milliliters of a one percent w/v acetone suspension of the test chemical to eight milliliters of water containing 0.05% of a surfactant, and for ascertaining dosage/mortality relationship, a series of further dosages were prepared by diluting the resulting mixture with appropriate further amounts of the surfactant solution. Preliminary dosage range-finding tests were followed by tests establishing dosage/mortality relationships, the latter being carried out on different days. A standard solution of 0.02% w/v of parathion in 0.05% of the solution, and appropriate dilutions thereof, also were used, for comparison. About 48 hours after the larvae were placed upon the plants, the numbers of dead and moribund larvae were noted, and the percent mortality was calculated. The toxicities of the test compounds were compared against those of the parathion standard and expressed as a toxicity index (J. Econ. Ent., 43, 45–53 (1950)) which was calculated as follows:

$$\text{Toxicity Index } (T.I.) = \frac{LC_{50} \text{ of standard}}{LC_{50} \text{ of test chemical}} \times 100$$

where "$LC_{50}$" is the concentration of the compound required to kill 50% of the larvae, as determined by plotting the dosage/mortality data on log probit paper.

The toxicity indexes for products of the invention were found to be:

| Compound No. | T.I. |
|---|---|
| 1 | 310 |
| 2 | 832 |
| 3 | 1988 |
| 4 | 720 |
| 5 | 1605 |
| 6 | 1084 |
| 7 | 1217 |
| 8 | 2211 |
| 9 | 583 |
| 10 | 630 |
| 11 | 429 |
| 12 | 2122 |
| 13 | 1915 |
| 14 | 718 |
| 15 | 1120 |
| 16 | 3026 |
| 17 | 1892 |

The invention includes within its scope insecticidal compositions comprising an adjuvant—that is, a carrier, optionally a surface-active agent—and, as active ingredient, at least one product of this invention. Likewise the invention includes also a method of combatting insect pests at a locus which comprises applying to the locus an effective amount of at least one product of the invention.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaprous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated caster oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the products of this invention to control insects comprises applying the product, ordinarily in a composition of one of the aforementioned types, to a locus or area to be protected from the insects, such as the foliage and/or the fruit of plants. The product of course is applied in an amount sufficient to exert the desired action. The dosage is dependent upon many factors, including the carrier employed, the method and conditions of the application, whether the formulation is present at the locus in the form of an aerosol, or as a film, or as discrete particles, the thickness of film or size of particles, and the like, proper consideration and resolution of these factors to provide the necessary dosage of active material at the locus to be protected being within the skill of those versed in the art. In general, however, the effective dosage of products of this invention at the locus to be protected—i.e., the dosage which the insect contacts—is of the order of 0.001 to 0.5% based on the total weight of the formulation, though under some circumstances the effective concentration will be as little as 0.0001% or as much as 2%, on the same basis.

We claim:

1. The product formed by reaction of tetrahydro-2-(nitromethylene) 2H-1,3-thiazine with an oxidized polysaccharide free from more than a minor amount of the carboxyl moiety.

2. The product according to claim 1 wherein the oxidized polysaccharide is an oxidized starch.

3. The product according to claim 1 wherein the oxadized starch is an oxidized microcrystalline cellulose.

4. The product according to claim 1 wherein the product is particulate in character, the largest dimension of each particle not exceeding about 100 microns.

5. A composition adopted for controlling corn earworms, which comprises an effective amount of a product of claim 1 together with an adjuvant therefor.

6. A method for protecting plant from attack by corn earworm larvae which comprises applying to the plants to be protected an effective dosage of a product of claim 1.

* * * * *